United States Patent
Itskovitz-Eldor et al.

(10) Patent No.: US 9,574,171 B2
(45) Date of Patent: Feb. 21, 2017

(54) METHODS OF GENERATING CORNEAL CELLS AND CELL POPULATIONS COMPRISING SAME

(75) Inventors: Joseph Itskovitz-Eldor, Haifa (IL); Daniel Aberdam, Nice (FR); Ruby Shalom-Feuerstein, Binyamina (IL)

(73) Assignees: TECHNION RESEARCH & DEVELOPMENT FOUNDATION LTD., Haifa (IL); INSTITUT NATIONAL DE LA SANTE ET DE LA RECHERCHE MEDICALE, Paris (FR)

(*) Notice: Subject to any disclaimer, the term of this patent is extended or adjusted under 35 U.S.C. 154(b) by 99 days.

(21) Appl. No.: 13/991,172

(22) PCT Filed: Dec. 1, 2011

(86) PCT No.: PCT/IL2011/000914
§ 371 (c)(1),
(2), (4) Date: Jun. 3, 2013

(87) PCT Pub. No.: WO2012/073238
PCT Pub. Date: Jun. 7, 2012

(65) Prior Publication Data
US 2013/0251692 A1 Sep. 26, 2013

Related U.S. Application Data

(60) Provisional application No. 61/418,915, filed on Dec. 2, 2010.

(51) Int. Cl.
*C12N 5/00* (2006.01)
*C12N 5/02* (2006.01)
*C12N 5/08* (2006.01)
*C07K 1/00* (2006.01)
*G01N 33/567* (2006.01)
*C12N 5/079* (2010.01)
*G01N 33/53* (2006.01)

(52) U.S. Cl.
CPC ......... *C12N 5/0062* (2013.01); *C12N 5/0621* (2013.01); *C12N 2501/11* (2013.01); *C12N 2501/155* (2013.01); *C12N 2501/33* (2013.01); *C12N 2502/085* (2013.01); *C12N 2502/1323* (2013.01); *C12N 2506/02* (2013.01); *C12N 2506/45* (2013.01); *C12N 2533/54* (2013.01); *C12N 2533/90* (2013.01); *G01N 33/53* (2013.01)

(58) Field of Classification Search
CPC ............ C12N 5/0621; C12N 2501/11; C12N 2501/33; C12N 2501/155; C12N 2506/02; C12N 2506/45; C12N 2502/085; C12N 2502/1323; C12N 2533/54; G01N 33/53
USPC ........ 435/7.21, 325, 366, 377, 405; 530/350
See application file for complete search history.

(56) References Cited

U.S. PATENT DOCUMENTS

2010/0233136 A1  9/2010  Aberdam et al.

FOREIGN PATENT DOCUMENTS

WO        2010/134619    11/2010
WO   WO 2012/073238     6/2012

OTHER PUBLICATIONS

Toschi et al., 2012, Journal of Tissue Engineering and Regenerative Medicine, vol. 6, Suppl. 1, pp. 460, Abstract No: IP1, 3rd TERMIS World Congress.*
Germain et al., 2004, IOVS, vol. 45, No. Suppl. 1, pp. U560, Annual Meeting of the Association for Research in Vision and Ophthalmology, Ft Lauderdale, FL.*
International Search Report and the Written Opinion Dated May 10, 2012 From the International Searching Authority Re. Application No. PCT/IL2011/000914.
Ahmad et al. "Differentiation of Human Embryonic Stem Cells Into Corneal Epithelial-Like Cells by In Vitro Replication of the Corneal Epithelial Stem Cell Niche", Stem Cells, 25: 1145-1155, Jan. 25, 2007. Abstract, p. 1146, col. 1, Para 3, p. 1150, col. 2, Para 3, p. 1151, col. 1, Para 2, Fig.4A, B, p. 1152, Fig.6C, D, p. 1153, col. 2, Para 1.
Blazejewska et al. "Corneal Limbal Microenvironment Can Induce Transdifferentiation of Hair Follicle Stem Cells Into Corneal Epithelial-Like Cells", Stem Cells, 27(3): 642-652, Mar. 2009. Abstract.
Gaggioli et al. "Fibroblast-Led Collective Invasion of Carcinoma Cells With Differing Roles for RhoGTPases in Leading and Following Cells", Nature Cell Biology, 9(12): 1392-1400, Dec. 2007 & Supplementary Information, p. 1-10, 2007.
Gambaro et al. "BMP-4 Induces a Smad-Dependent Apoptotic Cell Death of Mouse Embryonic Stem Cell-Derived Neural Precursors", Cell Death and Differentiation, 13: 1075-1087, Jul. 2006. p. 1077, col. 1, Para 3.
Homma et al. "Induction of Epithelial Progenitors In Vitro From Mouse Embryonic Stem Cells and Application for Reconstruction of Damaged Cornea in Mice", Investigative Ophthalmology & Visual Science, 45(12): 4320-4326, Dec. 2004.
Hu et al. "Neural Differentiation of Human Induced Pluripotent Stem Cells Follows Developmental Principles But With Variable Potency", Proc. Natl. Acad. Sci. USA, PNAS, 107(9): 4335-4340, Mar. 2, 2010. Abstract.
Larouche et al. "Regeneration of Skin and Cornea by Tissue Engineering", Stem Cells in Regenerative Medicine: Methods and Protocols, 482(Chap.15): 233-256, 2009.

(Continued)

*Primary Examiner* — Shin Lin Chen
(74) *Attorney, Agent, or Firm* — Whitham, Curtis & Cook, P.C.

(57) ABSTRACT

A method of generating a population of corneal epithelial cells is disclosed. The method comprises culturing human pluripotent stem cells in corneal fibroblast-conditioned medium on a solid surface comprising an extracellular matrix component thereby generating the population of corneal epithelial cells. Isolated cell populations and corneal tissues are also disclosed, as well as uses thereof.

8 Claims, 9 Drawing Sheets
(8 of 9 Drawing Sheet(s) Filed in Color)

(56) References Cited

OTHER PUBLICATIONS

Majo et al. "Oligoptoent Stem Cells Are Distributed Throughout the Mammalian Ocular Surface", 456: 250-255, Nov. 13, 2008.
Schwab et al. "Successful Transplantation of Bioengineered Tissue Replacements in Patients With Ocular Surface Disease", Cornea, 19(4): 421-426, Jul. 2000. p. 422, col. 1, Para 2, p. 423, cols. 1-2, p. 424, col. 1, Para 2-3.
Yoshida et al. "Cytokeratin 15 Can Be Used to Identify the Limbal Phenotype in Normal and Deseased Ocular Surfaces", Investigative Ophthalmology & Visual Science, 47(11): 4780-4786, Nov. 2006.
Yu et al. "Skin and Hair: Models for Exploring Organ Regeneration", Human Molecular Genetics, 17(R1): R54-R59, Apr. 15, 2008. p. R56, col. 1, Para 2.
International Preliminary Report on Patentability Dated Jun. 13, 2013 From the International Bureau of WIPO Re. Application No. PCT/IL2011/000914.
Supplementary European Search Report and the European Search Opinion Dated Aug. 4, 2014 From the European Patent Office Re. Application No. 11844229.2.
Cotsarelis et al. "Existence of Slow-Cycling Limbal Epithelial Basal Cells That Can Be Preferentially Stimulated to Proliferate: Implications on Epithelial Stem Cells", Cell, XP024246183, 57(2): 201-209, Apr. 21, 1989. Abstract.
Liu et al. "Enhancement of Long-Term Proliferative Capacity of Rabbit Corneal Epithelial Cells by Embryonic Stem Cell Conditioned Medium", Tissue Engineering Part C: Methods, XP055120989, 16(4): 793-802, Aug. 1, 2010. Abstract.
Shalom-Feuerstein et al. "Pluripotent Stem Cell Model Reveals Essential Roles for MiR-450b-5p and MiR-184 in Embryonic Corneal Lineage Specification", Stem Cells, XP055121056, 30(5): 898-909, Apr. 9, 2012.
Communication Pursuant to Rules 70(2) and 70a(2) EPC Dated Aug. 22, 2014 From the European Patent Office Re. Application No. 11844229.2.
Wolosin et al., "Ocular surface epithelial and stem cell development", Int. J. Dev. Biol. 48: 981-991 (2004).

\* cited by examiner

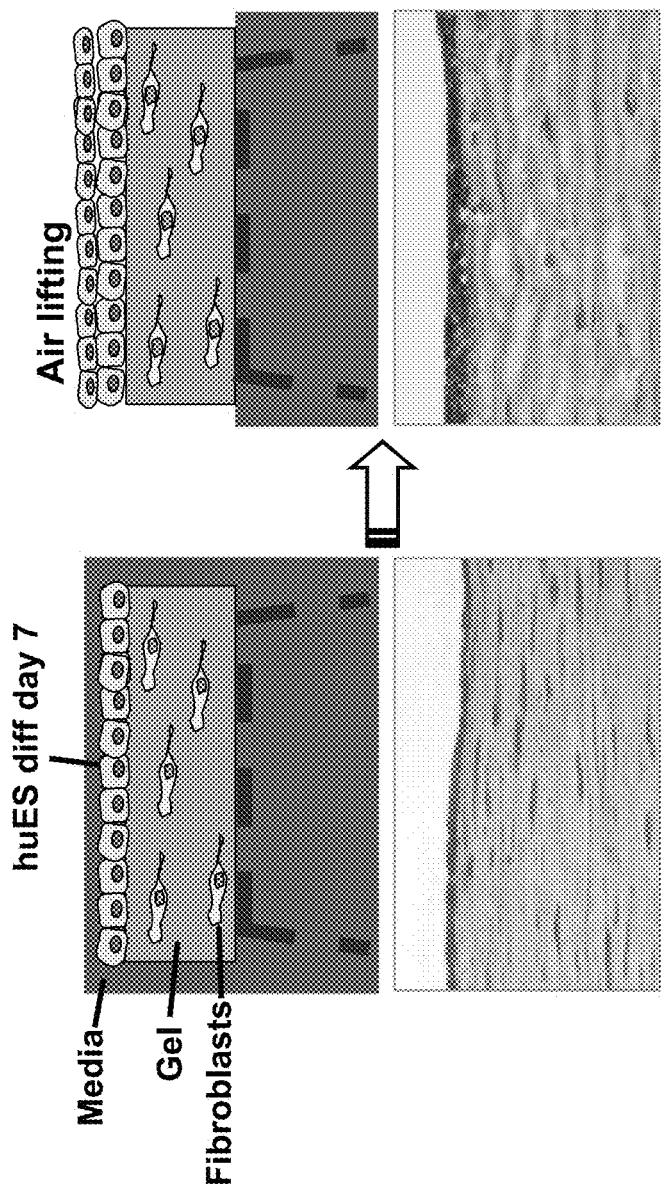

SEQUENCE LISTING

<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
gcttggtggt gtctttgtca      20

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
tcacacaacc gttggatacc      20

<210> SEQ ID NO 3
<211> LENGTH: 19
<212> TYPE: DNA
<213> ORGANISM: Artificial sequence

```
<220> FEATURE:
<223> OTHER INFORMATION: Single strand DNA oligonucleotide

<400> SEQUENCE: 3
gctgagccct gccaaagac                                                  19

<210> SEQ ID NO 4
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 4
gaggagcagc cattgaaata a                                               21
```

METHODS OF GENERATING CORNEAL CELLS AND CELL POPULATIONS COMPRISING SAME

RELATED APPLICATIONS

This application is a National Phase of PCT Patent Application No. PCT/IL2011/000914 having International filing date of Dec. 1, 2011, which claims the benefit of priority under 35 USC §119(e) of U.S. Provisional Patent Application No. 61/418,915 filed on Dec. 2, 2010. The contents of the above applications are all incorporated by reference as if fully set forth herein in their entirety.

SEQUENCE LISTING STATEMENT

The ASCII file, entitled 56481SequenceListing.txt, created on Apr. 29, 2013 comprising 1,276 bytes, submitted concurrently with the filing of this application is incorporated herein by reference.

FIELD AND BACKGROUND OF THE INVENTION

The present invention, in some embodiments thereof, relates to methods of generating corneal cells from pluripotent stem cells and cell populations comprising same.

The cornea is a unique, transparent structure that covers the iris, pupil, and anterior chamber, providing most of the eye's optical power. Together with the lens, the cornea refracts light and, as a result, aids in focusing. The cornea contributes more to the total refraction than the lens does, but, whereas the curvature of the lens can be adjusted to "tune" focus, the curvature of the cornea is fixed. The cornea has no blood vessels, its nourishment is obtained via diffusion from the tear fluid, the aqueous humor, and neurotrophins supplied by nerve fibers that innervate it. Thus, for example, disturbances in circulation of these fluids or inflammatory processes play a large role in the pathogenesis of corneal abnormalities.

The cornea is composed mostly of dense connective tissue. However, the collagen fibers are arranged in a parallel pattern, allowing light waves to constructively interfere, thus letting light pass through relatively uninhibited.

The corneal tissue is arranged in five basic layers: epithelium, Bowman's layer, stroma, Descemet's membrane and endothelium, each having a separate function. The epithelium is the outermost layer of the cornea, comprising about 10% of the tissue's thickness. The epithelium functions primarily to: (1) block passage of foreign materials, such as dust, water, and bacteria, into the eye and other layers of the cornea; and (2) provide a smooth surface that absorbs oxygen and cell nutrients from tears, then distributes these nutrients to the rest of the cornea. The corneal epithelium is maintained by stem cells (SCs) located at the periphery of the cornea, in a region known as the limbus. The corneal epithelium itself is devoid of its own stem cells. Limbal fibroblasts form the major cellular component of the limbal stroma upon which the LSCs reside, and they produce specific cytokines that promote corneal epithelial wound healing by the LSCs.

The changes associated with aging of the cornea include increased opacity, increased anterior surface curvatures, and possibly changes in refractive index distribution. Various refractive eye surgery techniques change the shape of the cornea in order to reduce the need for corrective lenses or otherwise improve the refractive state of the eye. In many techniques, reshaping of the cornea is performed by photoablation using an eximer laser.

If the corneal stroma develops visually significant opacity, irregularity, or edema, a cadaveric donor cornea can be transplanted.

Limbal auto-grafts have been applied to patients with a relatively high degree of success. In severe cases such as total limbal stem cell deficiency, allo-grafts may be obtained from patient's relatives or from post mortem donors. However, limbal tissue is highly immunogenic and the rate of graft rejection exceeds 35%, 5 years post transplantation. This method is further limited due to a shortage of donors. Further, living donors are at risk of developing limbal stem cell deficiency. To reduce this risk, a smaller limbal tissue may be grafted from donor and expanded ex vivo prior to transplantation. This technology does not allow treating patient immediately following injury, since it requires the cultivation of the cells for several weeks prior to grafting. Moreover, allogenic limbal stem cell transplantations to a patient are eventually rejected.

Synthetic corneas also exist (keratoprotheses), however, these are typically plastic inserts or may be composed of biocompatible synthetic materials that encourage tissue in-growth into the synthetic cornea, thereby promoting biointegration. Alternatively, orthokeratology offers the use of specialized hard or rigid gas-permeable contact lenses to transiently reshape the cornea in order to improve the refractive state of the eye or reduce the need for eyeglasses and contact lenses.

Homma et al. [Invest Ophthalmol Vis Sci. 2004 December; 45(12):4320-6] teach corneal epithelial differentiation of murine embryonic bodies on collagen IV-coated dishes.

Sajjad et al. [Stem Cells. 2007 May; 25(5):1145-55] teach generation of corneal epithelial-like cells by seeding human embryonic stem cells on collagen IV-coated dishes in the presence of medium that was conditioned by limbal fibroblasts. The resulting corneal epithelial cells were contaminated with skin cells.

SUMMARY OF THE INVENTION

According to an aspect of some embodiments of the present invention there is provided a method of generating a population of corneal epithelial cells comprising culturing human pluripotent stem cells in corneal fibroblast-conditioned medium on a solid surface comprising an extracellular matrix component thereby generating the population of corneal epithelial cells.

According to some embodiments of the invention, the corneal fibroblast-conditioned medium comprises bone morphogenetic protein-4 (BMP-4).

According to some embodiments of the invention, the human pluripotent stem cells comprise human embryonic stem cells (hESCs) or human induced pluripotent stem cells (hIPSCs).

According to some embodiments of the invention, the corneal fibroblast-conditioned medium comprises at least one agent selected from the group consisting of insulin, hydrocortisone and epidermal growth factor (EGF).

According to some embodiments of the invention, the corneal fibroblast-conditioned medium comprises insulin, hydrocortisone and epidermal growth factor (EGF).

According to some embodiments of the invention, the extracellular matrix component is selected from the group consisting of collagen IV, laminin, fibronectin and Matrigel®.

According to some embodiments of the invention, the method further comprises analyzing the population of corneal epithelial cells for at least one marker selected from the group consisting of keratin 3 (K3), keratin 12 (K12), paired box gene 6 (pax6), keratin 18 (K18) and Connexin 43.

According to some embodiments of the invention, the corneal fibroblast-conditioned medium is devoid of limbal fibroblasts.

According to some embodiments of the invention, there is provided an isolated population of human corneal epithelial cells generated according to the method of the present invention.

According to some embodiments of the invention, the isolated population of corneal epithelial cells does not comprise skin cells.

According to some embodiments of the invention, at least 70% of the cells of the population co-express K3 and Pax6.

According to some embodiments of the invention, less than 10% of the cells of the population express nanog and Oct4.

According to some embodiments of the invention, the isolated population of corneal epithelial cells is for use in treating an eye disorder.

According to some embodiments of the invention, there is provided a method of treating an eye disorder in a subject in need thereof, the method comprising transplanting to the subject a therapeutically effective amount of corneal epithelial cells generated according to the method of the present invention, thereby treating the eye disorder in the subject.

According to some embodiments of the invention, there is provided qa pharmaceutical composition comprising the isolated population of corneal epithelial cells of the present invention and a pharmaceutically acceptable carrier.

According to some embodiments of the invention, there is provided a method of generating corneal tissue, the method comprising:
  (a) dissociating the isolated population of human corneal epithelial cells of the present invention to generate a population of dissociated human corneal epithelial cells; and
  (b) culturing the dissociated human corneal epithelial cells on a scaffold under conditions that generate corneal tissue.

According to some embodiments of the invention, the scaffold comprises Matrigel® and collagen I.

According to some embodiments of the invention, the scaffold comprises a human amniotic membrane.

According to some embodiments of the invention, there is provided an isolated human corneal tissue generated according to the method of the present invention.

According to some embodiments of the invention, there is provided a human corneal tissue for use in treating an eye disorder.

According to some embodiments of the invention, there is provided a method of treating an eye disorder in a subject in need thereof, the method comprising transplanting to the subject a therapeutically effective amount of corneal tissue generated according to the method of the present invention, thereby treating the eye disorder in the subject.

According to some embodiments of the invention, there is provided a pharmaceutical composition comprising the isolated corneal tissue of the present invention and a pharmaceutically acceptable carrier.

According to an aspect of some embodiments of the present invention there is provided a method of screening for an agent which enhances differentiation towards a corneal epithelial lineage, the method comprising:
  (a) culturing human pluripotent stem cells in corneal fibroblast-conditioned medium on a solid surface comprising an extracellular matrix component in a presence of said agent; and
  (b) analyzing a differentiation status of said human pluripotent stem cells, wherein an increase in differentiation compared to a differentiation in an absence of said agent is indicative of an agent which enhances differentiation towards a corneal epithelial lineage.

According to some embodiments of the invention, the pluripotent stem cells comprise iPS cells.

According to some embodiments of the invention, the iPS cells are derived from healthy patients.

According to some embodiments of the invention, the iPS cells are derived from diseased patients.

According to some embodiments of the invention, the medium further comprises BMP-4.

According to some embodiments of the invention, the diseased patients are ectrodactyly-ectodermal dysplasia-cleft syndrome (EEC) patients.

According to some embodiments of the invention, the analyzing is effected by analyzing a morphology of said pluripotent stem cells.

According to some embodiments of the invention, the analyzing is effected by analyzing an expression of a corneal cell marker in said pluripotent stem cells.

According to some embodiments of the invention, the corneal cell marker is Pax6 or K3/K12.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings:

FIGS. 2A-C illustrate production of corneal epithelium from human ES cells. Corneal fibroblasts were embedded in collagen type 1 gel to produce a corneal stroma equivalent (A). After a week, huES-derived corneal cells were seeded on the top of the gel for one week to allow proliferation. Then, the culture was lifted up at the air-liquid interface to induce stratification (B). (C) Immunofluoresence analysis demonstrated that the resulting corneal epithelia were positive for K3 (red) and pax-6 (green; dapi in blue).

DESCRIPTION OF SPECIFIC EMBODIMENTS OF THE INVENTION

Figure 1A:
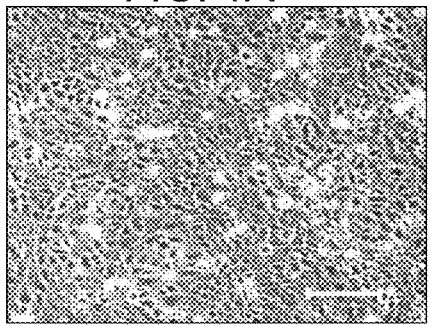
FIGS. 1A-G illustrate corneal commitment of human embryonic stem (huES) cells. (A). Morphology of a confluent human ES cell population after 10 days of corneal differentiation. (B-E) Kinetic analysis of corneal and pluripotent markers at different days of corneal differentiation of huES cells. Cells, RNA and protein extracts were collected at different times of commitment for qRT-PCR (B), Western blot (C), immunofluorescence (D) and FACS (E) analysis, showing efficient production of cornea-specific marker (pax-6, K12, K3, connexin 43) and disappearance of pluripotent-specific markers (oct-4 and nanog). (F and G) Specificity of the corneal differentiation of huES cells. (F) Corneal-specific DNA construct carrying the fluorescent GFP gene under the K12 promoter was transfected into several cell lines and human ES cells during corneal commitment and quantification was done by FACS analysis of GFP-positive cells. The corneal K12 promoter was active in human corneal epithelial control cells (HCE) and in huES committed cells at D6 and D12 and not in undifferentiated ES cells or non corneal epithelial cell lines (Hela, HaCaT). (G) Differentiated epidermal-specific markers K1, K10 and involucrin were not expressed by undifferentiated (D0) or huES cells committed into corneal differentiation (D6, D12 and D17), as compared to normal huma, keratinocytes (NHK), used as positive control.
Figure 1D:
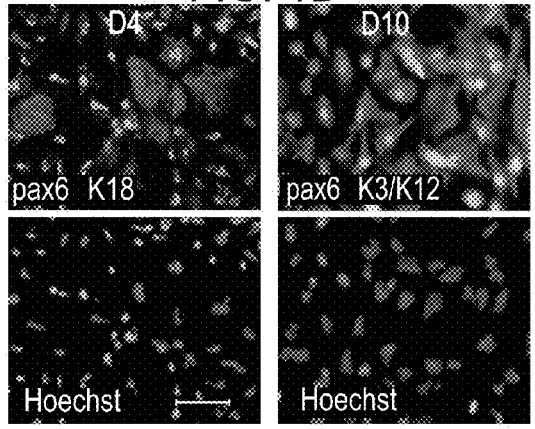

The present invention, in some embodiments thereof, relates to methods of generating corneal cells from pluripotent stem cells and cell populations comprising same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

When a cornea becomes cloudy due to disease or injury, light cannot penetrate the eye to reach the light-sensitive retina. Poor vision or blindness may result. Corneal transplant surgery involves the removal of the central portion of the cloudy cornea and replacing it with a clear cornea, usually donated through an eye bank. This technique is hampered by a scarcity of donors and graft rejection.

Limbal auto-grafts have been applied to patients with disorders of the cornea with a relatively high degree of success. In severe cases such as total limbal stem cell deficiency, allo-grafts may be obtained from patient's relatives or from post mortem donors. However, limbal tissue is highly immunogenic and the rate of graft rejection exceeds 35%, 5 years post transplantation. This method is further limited due to a shortage of donors. Further, living donors are at risk of developing limbal stem cell deficiency. To reduce this risk, a smaller limbal tissue may be grafted from donor and expanded ex vivo prior to transplantation. This technology does not allow treating patient immediately following injury, since it requires the cultivation of the cells for several weeks prior to grafting. Moreover, allogenic limbal stem cell transplantations to a patient are eventually rejected.

In order to overcome these problems, the present inventors devised a technique whereby they generated corneal epithelial cell populations from pluripotent stem cells. The differentiation protocol relies on the use of corneal fibroblast-conditioned medium.

As illustrated in FIGS. 1A-G, the generated corneal epithelial cell population was homogeneous, the cells expressing K3, K12, pax6 and Connexin43. Furthermore, the present inventors noted that the cell population was devoid of cells expressing epidermal markers such as K1, K10 and Involucrin (see FIG. 1G).

The present inventors further showed that 3D culture of such cells resulted in the generation of corneal tissue equivalents (FIG. 2). This procedure allows the production of ready to use tissues for corneal transplantation, thereby resolving the need of donors.

Thus, according to one aspect of the present invention there is provided a method of generating a population of corneal epithelial cells comprising culturing human pluripotent stem cells in corneal fibroblast-conditioned medium on a solid surface comprising an extracellular matrix component thereby generating the population of corneal epithelial cells.

The method of the present invention is initially effected by obtaining pluripotent stem cells and culturing them.

As used herein, the phrase "stem cells" refers to cells which are capable of remaining in an undifferentiated state (e.g., pluripotent or multipotent stem cells) for extended periods of time in culture until induced to differentiate into other cell types having a particular, specialized function (e.g., fully differentiated cells). The phrase "pluripotent stem cells" encompasses embryonic stem cells (ESCs) and induced pluripotent stem cells (iPS. The stem cells are typically mammalian pluripotent cells, such as for example human pluripotent stem cells.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763) and embryonic germ (EG) cells which are obtained from the genital tissue of a fetus any time during gestation, preferably before 10 weeks of gestation.

Induced pluripotent stem cells (iPS; embryonic-like stem cells), are cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin or hair) and undergo de-differentiation by genetic manipulation which re-program the cell to acquire embryonic stem cells characteristics. According to some embodiments of the invention, the induced pluripotent stem cells are formed by inducing the expression of Oct-4, Sox2, Kfl4 and c-Myc in a somatic stem cell.

The embryonic stem cells of the present invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used with this aspect of the present invention. Human ES cells can be purchased from the NIH human embryonic stem cells registry (www.escr.nih.gov). Non-limiting examples of commercially available embryonic stem cell lines are BG01, BG02, BG03, BG04, CY12, CY30, CY92, CY10, TE03 and TE32.

In addition, ES cells can be obtained from other species as well, including mouse (Mills and Bradley, 2001), golden hamster [Doetschman et al., 1988, Dev Biol. 127: 224-7], rat [Iannaccone et al., 1994, Dev Biol. 163: 288-92] rabbit [Giles et al. 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, Mo., USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

Induced pluripotent stem cells (iPS) (embryonic-like stem cells) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripotent Stem Cells from Adult Mouse Liver and Stomach Cells. Science. 2008 Feb. 14. (Epub ahead of print); IH Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear transfer into zygotes if the recipient cells are arrested in mitosis.

It will be appreciated that undifferentiated stem cells are of a distinct morphology, which is clearly distinguishable from differentiated cells of embryo or adult origin by the skilled in the art. Typically, undifferentiated stem cells have high nuclear/cytoplasmic ratios, prominent nucleoli and compact colony formation with poorly discernable cell junctions. Additional features of undifferentiated stem cells are further described hereinunder.

Currently practiced ES culturing methods are mainly based on the use of feeder cell layers which secrete factors needed for stem cell proliferation, while at the same time, inhibit their differentiation. Feeder cell free systems have also been used in ES cell culturing, such systems utilize matrices supplemented with serum, cytokines and growth factors as a replacement for the feeder cell layer.

In order to induce differentiation of the pluripotent stem cells to the corneal epithelial lineage, the pluripotent stem cells are cultured in corneal fibroblast-conditioned medium.

Corneal fibroblasts may be obtained from cadavers or living donors. According to one embodiment, the corneal fibroblasts are obtained from humans. Typically corneal fibroblasts are isolated by incubation of the cornea with a dispersing agent (e.g. Dispase II, typsin or collagenase for about 1-18 hours at 37° C.). The epithelial sheet may then be removed with forceps. Care should be taken to avoid contamination of the corneal sample with limbal tissue, such that the cells used to generate the conditioned medium are not contaminated with limbal fibroblasts.

Conditioned medium is the growth medium of a monolayer cell culture (i.e., feeder cells) present following a certain culturing period. The conditioned medium includes growth factors and cytokines secreted by the monolayer cells in the culture.

In order to produce corneal fibroblast conditioned medium, the isolated fibroblasts may initially be expanded by culturing in a suitable medium (e.g. dulbeco's modified eagle medium (DMEM) supplemented with 10% new born calf serum). When the fibroblast cell population reaches about 80%-100% density (see FIG. 2A), cell proliferation is stopped, e.g. by incubation in mitomycin C (8 µg/ml) for about three hours. The mitomycinized cells are then incubated in a suitable growth medium.

Conditioned medium is collected from the corneal fibroblasts forming monolayers in culture.

The growth medium can be any medium suitable for culturing the corneal fibroblasts. The growth medium can be supplemented with nutritional factors, such as amino acids, (e.g., L-glutamine), anti-oxidants (e.g., beta-mercaptoethanol) and growth factors, which benefit corneal fibroblast cell growth.

According to one embodiment bone morphogenetic protein-4 (BMP-4) may be added during the culture period. The BMP-4 may be added for the entire length of the culturing period or at a particular stage of the culturing period (e.g. for the first three days of the culturing period).

An exemplary concentration of BMP-4 is between about 0.1-10 nM, more preferably between 0.1-5 nM, more preferably between about 0.1 and 1 nM (for example 0.5 nM).

According to one embodiment, the growth medium comprises at least one of the following agents—insulin (e.g. 5 µg/ml), hydrocortisone (e.g. 0.5 µg/ml) and EGF e.g. (10 ng/ml).

According to another embodiment the growth medium comprises insulin, hydrocortisone and EGF.

An exemplary medium is epithelial medium ((DMEM 60%, HamF12 30%, FCII 10%, insulin 5 µg/ml, hydrocortisone 0.5 µg/ml, EGF 10 ng/ml, 0.2 mM Adenine, 10 nM Cholera toxin).

The epithelial fibroblast cells are cultured in the growth medium for sufficient time to allow adequate accumulation of secreted factors to support stem cell differentiation towards the corneal epithelial cell lineage. Typically, the medium is conditioned by culturing for 4 hours at 37° C. to 24 hours.

However, the culturing period can be scaled by assessing the effect of the conditioned medium on stem cell differentiation.

Selection of culture apparatus for conditioning the medium is based on the scale and purpose of the conditioned medium. Large-scale production preferably involves the use of dedicated devices. Continuous cell culture systems are reviewed in Furey (2000) Genetic Eng. News 20:10.

Following accumulation of adequate factors in the medium, growth medium (i.e., conditioned medium) is separated from the corneal fibroblasts and collected. It will be appreciated that the corneal fibroblasts can be used repeatedly to condition further batches of medium over additional culture periods, provided that the cells retain their ability to condition the medium.

According to one embodiment, the medium is collected every day and replaced by fresh media for up to 10 days.

Preferably, the conditioned medium is sterilized (e.g., filtration using a 20 µM filter) prior to use. The conditioned medium of some embodiments of the invention may be applied directly on stem cells or extracted to concentrate the effective factor such as by salt filtration. For future use, conditioned medium is preferably stored frozen at −80° C.

Culturing in corneal fibroblast-conditioned medium is typically effected on a solid surface which comprises an extracellular matrix component. Examples of extracellular matrix components include but are not limited to collagen IV, laminin, fibronectin and Matrigel®.

Methods of coating culture dishes with extraceullar matrix components are well known in the art and further described in the Examples section herein below.

The pluripotent stem cells are cultured under suitable conditions to allow differentiation. According to one embodiment, the cells are cultured for about 5 days, 7 days or about 10 days.

The differentiation status of the cells may be determined by analyzing marker expression thereof. Thus for example the following markers may be analyzed: cytokeratin 3 (K3), cytokeratin 12 (K12), paired box gene 6 (pax6), cytokeratin 18 (K18) and Connexin 43. Expression of the above described markers in at least 50%, at least 60%, at least 70%, at least 80%, at least 90% of the generated cell population may be used as an indication that the cell population is differentiated towards the corneal epithelial lineage.

According to a particular embodiment, the population of cells is selected wherein at least 70%, 80% or 90% of the cells of the population co-express K3 and Pax6. Alternatively, or additionally, the differentiation status of the cells may be determined by analyzing markers of undifferentiated stem cells, such as Oct4 or nanog. Expression of the above described markers in less than 40%, less than 30%, less than 20%, less than 10%, less than 5% of the generated cell population may be used as an indication that the cell population comprises differentiated cells.

Preferably the generated population of cells does not comprise skin cells. Accordingly, the population of cells may be analyzed for skin cell markers (e.g. K1, K10 and Involucrin) and only cell populations which do not express such markers (e.g. less than 10% of the cells express or less than 5% of the cells express) are selected.

Methods for analyzing cells for particular markers are well known in the art and include for Example Western Blot Analysis, flow cytometry and reverse transcriptase PCR analysis (RT-PCR). Immunohistochemistry techniques may be used to ascertain whether a particular cell co-expresses two or more markers.

Antibodies for K3, K12, Pax6, K18, K1, K10, involucrin and connexin 43 are commercially available from Companies such as Santa Cruz Biotechnology and Chemicon.

Exemplary primer sequences which may be used to analyze the differentiation status of the cells are provided herein below.

```
Pax-6 (forward):
                                          (SEQ ID NO: 1)
gCTTggTggTgTCTTTgTCA Pax-6 (reverse):
                                          (SEQ ID NO: 2)
TCACACAACCgTTggATACC connexin 43 (forward):
                                          (SEQ ID NO: 3)
gCTgAgCCCTgCCAAAgAC connexin 43 (reverse):
                                          (SEQ ID NO: 4)
gAggAgCAgCCATTgAAATAA
```

The differentiation status of the cells may also be determined by analyzing promoter activity for a particular gene known to be expressed in differentiated cells. Example 1 of the Examples section herein below details how the activity of the k12 promoter (a corneal specific promoter) may be analyzed in the differentiated cell populations.

The above described differentiation protocol may be used to screen for agents which enhance differentiation towards a corneal epithelial lineage.

Thus, according to another aspect of the present invention, there is provided a method of screening for an agent which enhances differentiation towards a corneal epithelial lineage, the method comprising:

(a) culturing human pluripotent stem cells in corneal fibroblast-conditioned medium on a solid surface comprising an extracellular matrix component in a presence of said agent; and (b) analyzing a differentiation status of the human pluripotent stem cells, wherein an increase in differentiation compared to a differentiation in an absence of the agent is indicative of an agent which enhances differentiation towards a corneal epithelial lineage.

Analyzing the differentiation status of the cells has been described herein above.

The pluripotent stem cells may be embryonic stem cells or induced pluripotent stem cells (iPS cells). The iPS cells may be derived from healthy subjects or patients who have a disease which affects corneal epithelial cells—for example, ectrodactyly-ectodermal dysplasia-cleft syndrome (EEC) patients. The present inventors have shown that iPS cells derived from such patients do not undergo differentiation to corneal epithelial cells to the same extent as iPS cells derived from healthy subjects. Thus, the present protocol may be used to screen for a drug that enhances corneal epithelial cell differentiation for the treatment of a particular disease.

Examples of agents that may be screened include polypeptide agents, polynucleotide agents, small molecule agents and other chemicals.

The isolated cell populations generated according to the method of this aspect of the present invention may be used for various applications including transplantation thereof for the treatment of diseases or disorders of the cornea, as further described herein below. In addition, the isolated cell populations may be used as a cellular model for drug discovery and cell toxicity tests. The reproducibility of identical cells from the same source will allow comparative and standardizes studies, which is an important criteria for industrials of cosmetology and pharmacology.

Alternatively, the isolated cell populations (e.g. ones that have been initially differentiated for 1-2 weeks in the corneal fibroblast conditioned medium) may be further differentiated on a 3D scaffold to generate corneal tissue.

According to one embodiment, the corneal tissue is stratified.

According to another embodiment, the corneal tissue comprises at least 3 layers of corneal epithelial tissue.

According to another embodiment the corneal tissue is devoid of squamous cells.

A method of generating corneal tissue on a scaffold is described in Example 2 of the Examples section below and illustrated in FIGS. 3A-I.

According to one embodiment the 3D scaffold comprises a gel composed of Matrigel® and collagen I.

According to another embodiment, the scaffold comprises a human amniotic membrane.

Such techniques are described in Koizumi et al., Investigative Ophthalmology & Visual Science, August 2000, Vol. 41, No. 9; Gaggioli et al., Nature cell biology volume 9, number 12, 2007 and Larouch et al., Chapter 15, Stem Cells in Regenerative Medicine: Methods and Protocols, vol. 482, 2009), the contents of each being incorporated by reference.

Typically, the cell populations are differentiated on the scaffold for about 1-2 weeks to induce differentiation of corneal tissue.

As mentioned, the isolated corneal epithelial cell populations (and the corneal tissue differentiated therefrom) may be used to treat diseases and disorders of the cornea.

Disorders affecting the cornea include, but are not limited to, allergies, conjunctivitis, corneal infections, dry eye, Fuchs' dystrophy, herpes zoster, iridocorneal endothelial syndrome, keratoconus, lattice dystrophy, map-dot-fingerprint dystrophy, ocular herpes, Stevens-Johnson syndrome, pterygium, keratitis, corneal ulcer, corneal abrasion, snow blindness, arc eye, Thygeson's superficial puncate keratopathy, and keratpconjunctivitis sicca.

In corneal transplant surgery, the surgeon typically removes the central portion of the diseased or injured cornea and replaces it with a clear cornea. The new cornea or corneal cells are placed in the opening and is sutured to the eye (see, e.g., Rapuano et al. Anterior Segment, The Requisites (Requisites in Ophthalmology), 1999, Mosby, Inc., Philadelphia, Pa.). Typically about $1-2 \times 10^6$ cells/eye are transplanted to the damaged cornea.

In one embodiment, a method for replacement of a cornea of an eye using the synthetic cornea of the present invention includes surgically excising the cornea from the eye, inserting the synthetic cornea into the area of the removed cornea, and allowing the synthetic cornea to interface with tissue underlying the excision to anchor the synthetic cornea to the eye.

In a related aspect, the method includes separating a portion of the outer surface of a cornea thereby forming a corneal flap and a corneal bed, the corneal flap having an anterior surface and a posterior surface, the corneal bed having a shaped anterior surface, implanting the synthetic cornea on the corneal bed, the cornea having an anterior surface and a posterior surface, and replacing the portion of the cornea that was separated.

Careful histological and immunohistochemical analysis should be performed at different times following grafting by using specific markers. The number of goblet cells on the corneal surface should be evaluated with impression cytology to evaluate the presence of limbal deficiency. The rejection index, the mean survival time, and the rejection rates may be calculated for each group.

As mentioned hereinabove, the corneal cells or tissue of the present invention can be derived from either autologous sources (induced pluripotent stem cells) or from allogeneic sources such as embryonic stem cells. Since non-autologous cells are likely to induce an immune reaction when administered to the body several approaches have been developed to reduce the likelihood of rejection of non-autologous cells. For example, prior to transplantation, the histo-compatibility of the subject may be tested such that only histo-compatible corneal grafts may be transplanted.

Other approaches include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylideneacetate). J. Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Thechnol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 µm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

If appropriate, the patient can be further treated with pharmaceutical agents or bioactives that facilitate the survival and function of the transplanted cells. These agents may include, for example, insulin, members of the TGF-beta family, including TGF-beta1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -7, -8, -10, -15), vascular endothelial cell-derived growth factor (VEGF), pleiotrophin, endothelin, among others. Other pharmaceutical compounds can include, for example, nicotinamide, glucagon like peptide-I (GLP-1) and II, GLP-1 and 2 mimetibody, Exendin-4, retinoic acid, parathyroid hormone, MAPK inhibitors, such as, for example, compounds disclosed in U.S. Published Application 2004/0209901 and U.S. Published Application 2004/0132729.

The cells or tissue of the present invention may be transplanted to a human subject per se, or in a pharmaceutical composition where it is mixed with suitable carriers or excipients.

As used herein a "pharmaceutical composition" refers to a preparation of one or more of the cell populations described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Pharmaceutical compositions suitable for use in context of the present invention include compositions wherein the active ingredients are contained in an amount effective to achieve the intended purpose. More specifically, a therapeutically effective amount means an amount of active ingredients (corneal cells) effective to prevent, alleviate or ameliorate symptoms of a disorder.

Determination of a therapeutically effective amount is well within the capability of those skilled in the art, especially in light of the detailed disclosure provided herein.

For any preparation used in the methods of the invention, the therapeutically effective amount or dose can be estimated from animal models to achieve a desired concentration or titer. Such information can be used to more accurately determine useful doses in humans.

Toxicity and therapeutic efficacy of the active ingredients described herein can be determined by standard pharmaceutical procedures in experimental animals. The data obtained from these animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide cell numbers sufficient to induce repair or improve sight (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Differentiation of Human Embryonic Stem Cells to Corneal Cells

I. Preparation of corneal fibroblasts conditioned epithelial medium: To prepare conditioned media, primary corneal fibroblasts were extracted from human cornea that is not suitable for transplantation by incubation of the cornea with Dispase II (2 mg/ml) overnight at 37° C. The epithelial sheet was removed and the fibroblasts were cultured in culture dishes in dulbeco's modified eagle medium (DMEM) supplemented with 10% new born calf serum. When the fibroblast cell population reached 80%-100% density (see FIG. 2A), cell proliferation was stopped by incubating in mitomycin C (8 μg/ml) for three hours. To obtain conditioned media, the mitomycinized cells were incubated with epithelial media ((DMEM 60%, HamF12 30%, FCII 10%, insulin 5 μg/ml, hydrocortisone 0.5 μg/ml, EGF 10 ng/ml, 0.2 mM Adenine, 10 nM Cholera toxin). The medium was collected every day and replaced by fresh media for up to 10 days. The medium was filtered and stored at −20° C. until use.

II. Coating of culture dishes: Culture dishes were incubated with collagen IV (0.5 mg/ml) or matrigel (0.25 mg/ml) at 37° C. for 4 hours and then washed extensively with phosphate buffered saline.

III. Differentiation of pluripotent stem cells into corneal epithelial lineage: Pluripotent stem cell cells were incubated with collagenase (2 mg/ml) for 1 hour and then colonies were seeded on collagen IV or matrigel-coated dishes. Medium was replaced every second day by fresh corneal fibroblast conditioned epithelial media for about two weeks.

Real-time PCR analysis: RNA extractions of cells during different time point of corneal differentiation were analyzed by real-time PCR analysis of K18, K12, pax6, GAPDH.

Western blot analysis: we used anti K3/K12 Ab, anti pax6 Ab, anti K18 Ab, anti Connexin 43 Ab, anti Nanog Ab, anti Oct4 Ab.

FACS analysis: FACS analysis was performed using anti K18 Ab, anti K3/K12 Ab and anti pax6 Ab.

Transfection of cells with GFP under a K12 promoter: Embryonic stem cells-derived corneal cells (at Day 10 of differentiation), and cells that were used as positive (Human corneal epithelial (HCE) immortalized cell line) or negative (HaCaT, Hela, undifferentiated ES cells) controls were transfected with a GFP-encoding plasmid that is under K12-corneal specific promoter, using Fugene reagent according the manufacturer instructions. After 48 hours, the percentage of cells with GFP fluorescence was examined by FACS analysis.

Results

Figure 1B:
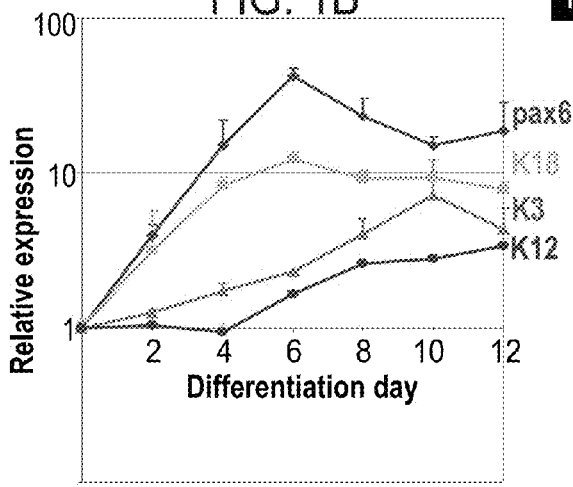
Figure 1C:
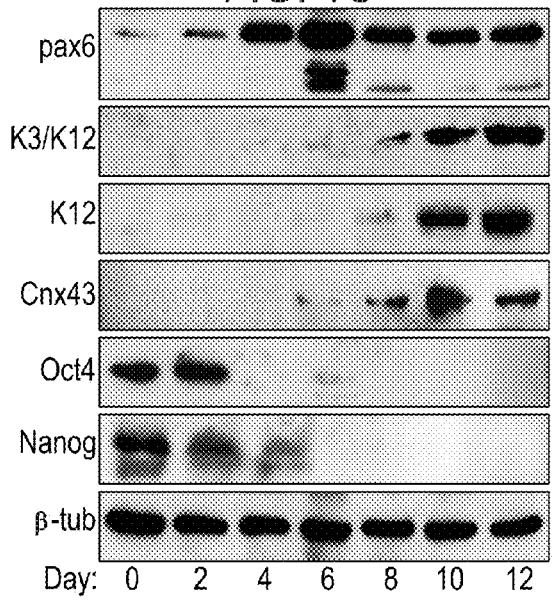

The morphology of the differentiated cells appeared relatively homogenous at day 9, as shown in FIG. 1A. Corneal differentiation was evaluated by quantitative real time polymerase chain reaction (qPCR) of corneal epithelial markers (FIG. 1B). Elevated levels of the ectodermal marker K18 (and K8, not shown), and of pax6, a key factor in eye and corneal development, were recorded in early culture days. The mRNA levels of corneal specific cytokeratins, namely K12 and K3 were increased at late culture days (FIG. 1B).

Western blot analysis demonstrated that the protein levels of known corneal-epithelial markers (namely, pax6, K3, K12 and Connexin43) increased gradually at late differentiation stages while embryonic stem cell markers (Nanog and Oct4) became undetectable within 6-8 days (FIG. 1C), suggesting that this protocol induces efficient corneal differentiation of ES cells.

The co-expression of K18 and pax6 hallmarks the 'lens placode', a structure that emerges at day 9.5 of mouse embryogenesis (E9.5), from which the corneal epithelium is derived. At later embryonic stages, the corneal epithelium maintains pax6-expression and begins to express K12 and K3. Notably, the majority of the cells at day 4 of ES differentiation expressed K18 or co-expressed K18 and pax6 (FIG. 1D, left panel), while, at day 10 of ES differentiation, the majority of cells co-expressed K3 and pax6 (FIG. 1D), suggesting that ES cells differentiate into corneal precursors in a manner that reminiscent of corneal embryogenesis.

Figure 1E:
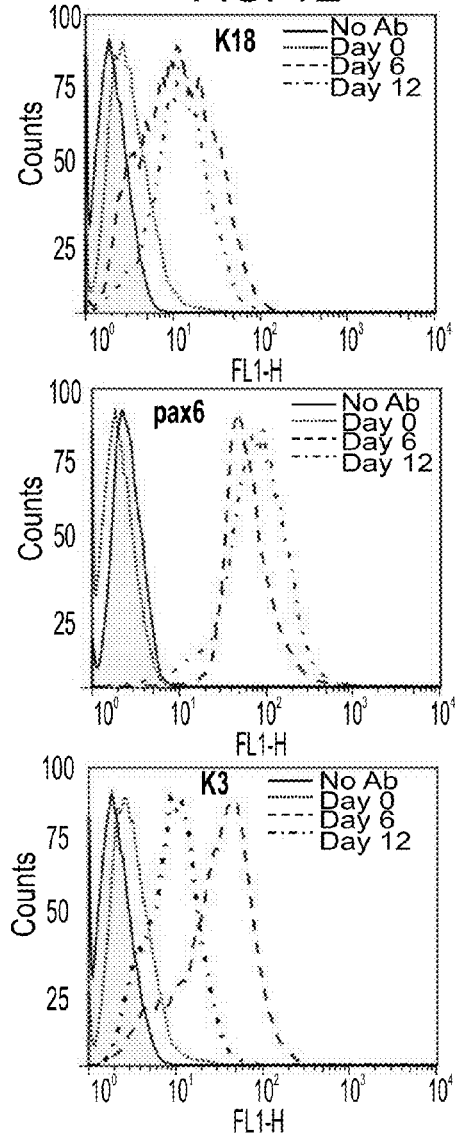
Figure 1F:
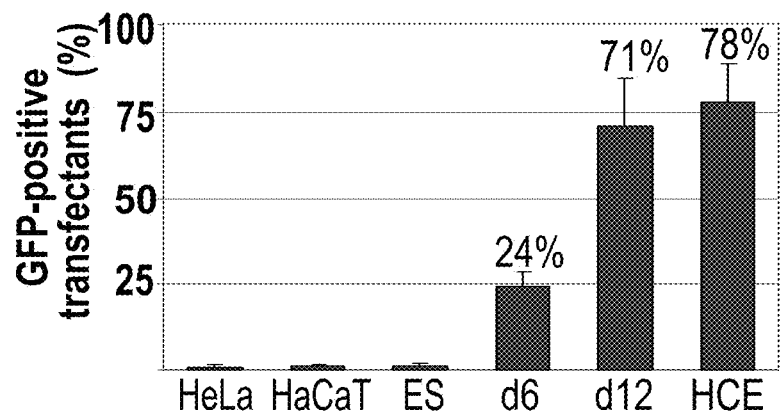
Figure 1G:
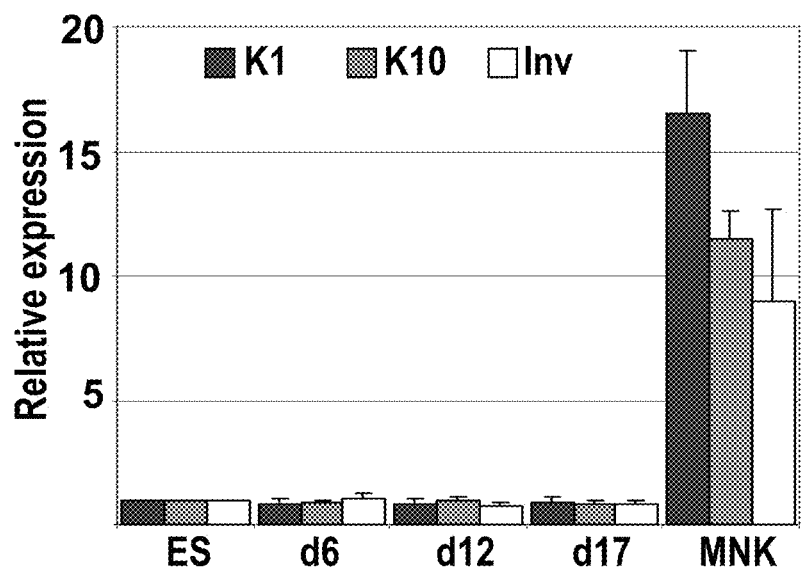
Figure 3A:
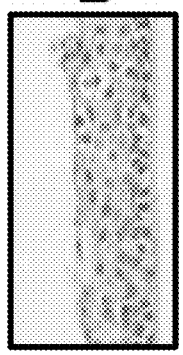
FIGS. 3A-C are photographs illustrating production of corneal epithelial tissue using amniotic membrane as a scaffold.
Figure 3B:
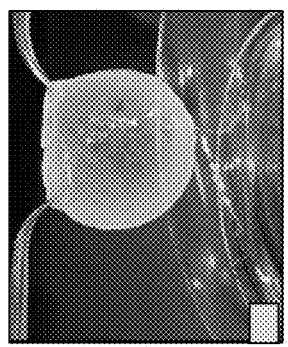
Figure 3C:
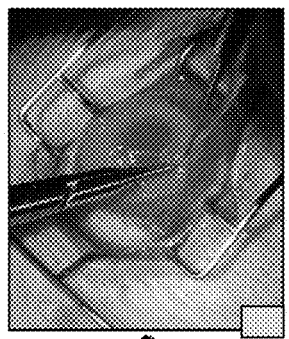

To further assess corneal epithelial fate, differentiated cells were subjected to FACS analysis of K18, pax6 and K3. As shown in FIG. 1E, most of the cells expressed K18 and pax6 at day 6, while the vast majority of the cells expressed K3 and pax6 (>90%) at day 12. Furthermore, the encoding sequence for green fluorescent protein (GFP) was cloned under the corneal-specific promoter of K12 gene, which is the most specific amongst corneal markers. The specificity of this construct to corneal epithelial cells was confirmed by the transfection of various non-corneal cell lines as negative controls (Hela, HaCaT, ES) or of a human corneal epithelial cell line (HCE) as positive control (FIG. 1F). While non-corneal cells did not express any significant amount of GFP, 78% of HCE and 71% of ES-derived corneal epithelial-like (ES-EC) cells displayed a strong K12-promoter activity (FIG. 1F). Finally, no epidermal differentiation markers (namely K1, K10 and Involucrin, see FIG. 1G) were detected, suggesting that highly enriched population of ES-CE cells were obtained that was not contaminated with epidermal-like cells.

Example 2

Generation of Corneal Tissue from Embryonic Stem Cells

Materials and Methods

After 1-2 weeks of differentiation of pluripotent stem cells on collagen IV or matrigel in the presence of conditioned media, cells were collected by dispase or trypsin and reseeded onto a corneal stroma equivalent gels in a 3D organotypic reconstitution assay: primary human corneal fibroblast cells were embedded in gels that were composed of matrigel and collagen I, and hES-derived corneal cells were seeded on top of these gels in epithelial media. Corneal stratification was induced by air-liquid interphase as illustrated in FIGS. 2A-C and further exemplified in Gaggioli et al., Nature cell biology volume 9, number 12, 2007. Then air liquid interface was induced by reducing media inside the inserts and cells were allowed to stratify for 1-2 weeks, while medium was replaced every day. Alternatively, differentiated cells were seeded on human amniotic membrane and lifted from the culture (as described for instance in Koizumi et al., Investigative Ophthalmology & Visual Science, August 2000, Vol. 41, No. 9).

Example 3

Differentiation of Human Induced Pluripotent Stem (iPS) Cells to Corneal Cells

I. Preparation of corneal fibroblasts conditioned epithelial medium: as described in Example 1.

II. Coating of culture dishes: as described in Example 1.

III. Differentiation of iPS cells into corneal epithelial lineage: iPS derived from human hair follicle cells or dermal fibroblasts were seeded on collagen IV or matrigel-coated dishes. Medium was replaced every second day by fresh corneal fibroblast conditioned epithelial media for about two weeks. On days 3, 8 and 14, BMP-4 was added to the medium.

Real-time PCR analysis: RNA extractions of cells during different time point of corneal differentiation were analyzed by real-time PCR analysis of K3, K14, K12, K18, pax6 and DNp63.

FACS analysis: FACS analysis was performed using anti K14 Ab, anti K3/K12 Ab and anti pax6 Ab.

Results

Figures 4A, 4B:
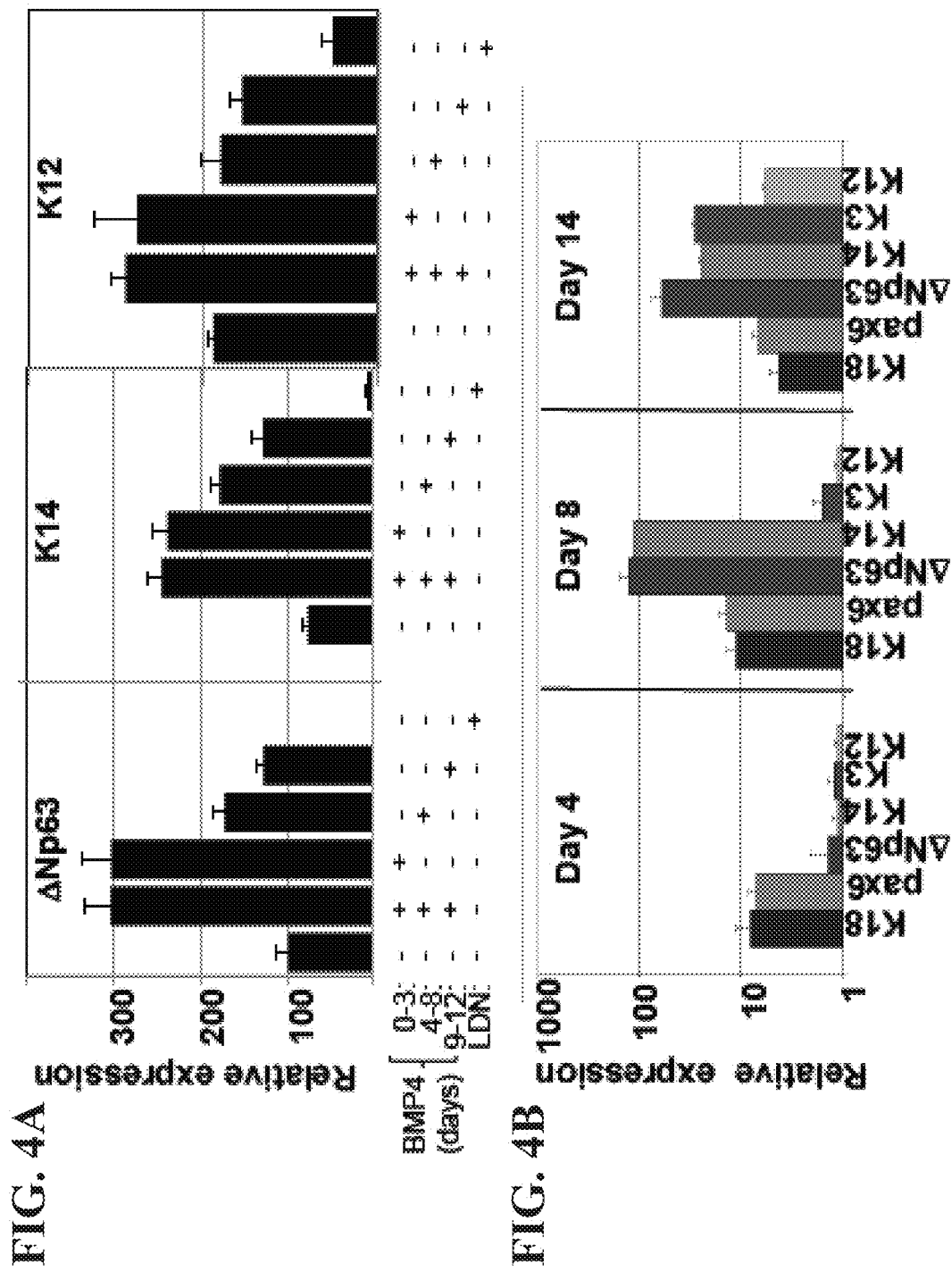
FIGS. 4A-C are graphs illustrating differentiation of iPSC cells into corneal epithelial lineage. iPSC colonies were seeded on collagen IV-coated dishes in the presence of epithelial-medium that was conditioned by corneal fibroblasts. (A). RNA preparations obtained in the indicated days of corneal differentiation were subjected to real time PCR analysis of the indicated genes. The mRNA expression levels were normalized to GAPDH. Data represents the relative fold change of each transcript as compared to its levels as recorded in undifferentiated hES cells. (B). Test of BMP-4. (C). Corneal commitment of hair follicle-derived iPSCs (HF2-iPS), fibroblast-derived iPSCs (DF1 and DF2-iPS) and human ES cells quantified by real time qRT-PCR analysis for K18, pax6, DNp63, K14 and K3 genes.
Figure 4C:
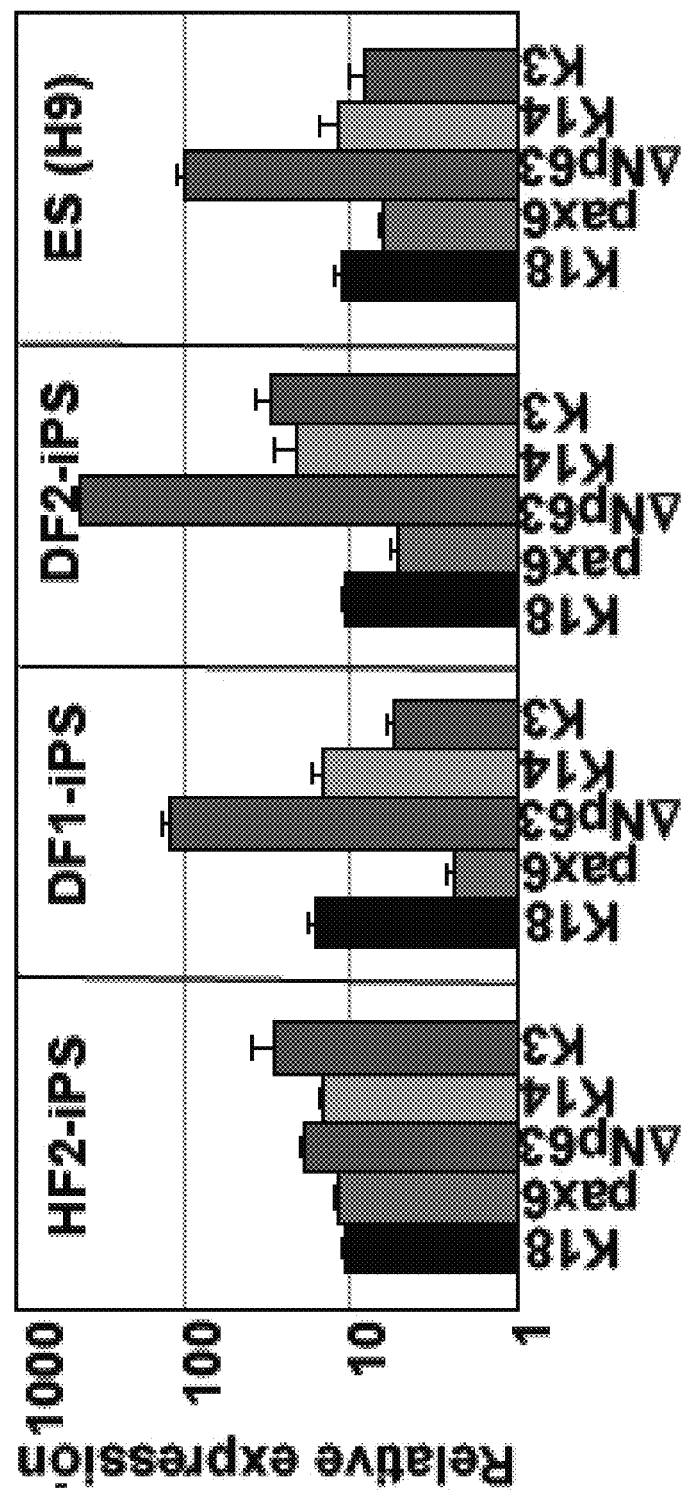

Addition of BMP-4 during the first three days significantly enhanced corneal differentiation, as illustrated by increased expression of DNp63, K14 and K12 (FIG. 4A). This effect was inhibited by LDN, a specific antagonist of BMP-4. To follow corneal commitment, messenger RNA levels of corneal epithelial lineage genes were recorded at different time points in the course of iPSCs differentiation by qPCR (FIG. 4B). Elevation in ectodermal marker K18 (and K8, not shown) appeared already within 2-4 culture days (FIG. 4B), along with the expression of pax6, an early marker of neuroectodermal cell fate and a key regulator of eye development. Early epithelial commitment was detected at days 6-8 by the expression of limbal markers, p63 and K14, while markers of mature corneal epithelium (K3, K12) and Connexin 43 (not shown) appeared within 10-14 days (FIG. 4B). Simultaneous expression of K18 and pax6 at early stage recapitulated the in vivo co-expression in the lens placode at E9.5, was followed by co-expression of pax6 and K3 which are hallmark of mature corneal cells. The robustness of corneal epithelial-like cell production was evaluated at day 12 by FACS analysis. The vast majority of the cells expressed K3 (>90%) while 20% of the cells remained K14-positive cells. Finally, although epidermal marker K10 increased at the mRNA levels, no K10 protein could be detected (not shown). Similar results were obtained with iPSCs derived from human fibroblasts or huESCs (FIG. 4C).

Example 4

Differentiation of Diseased iPS Cells Towards a Corneal Fate

Figure 5A:
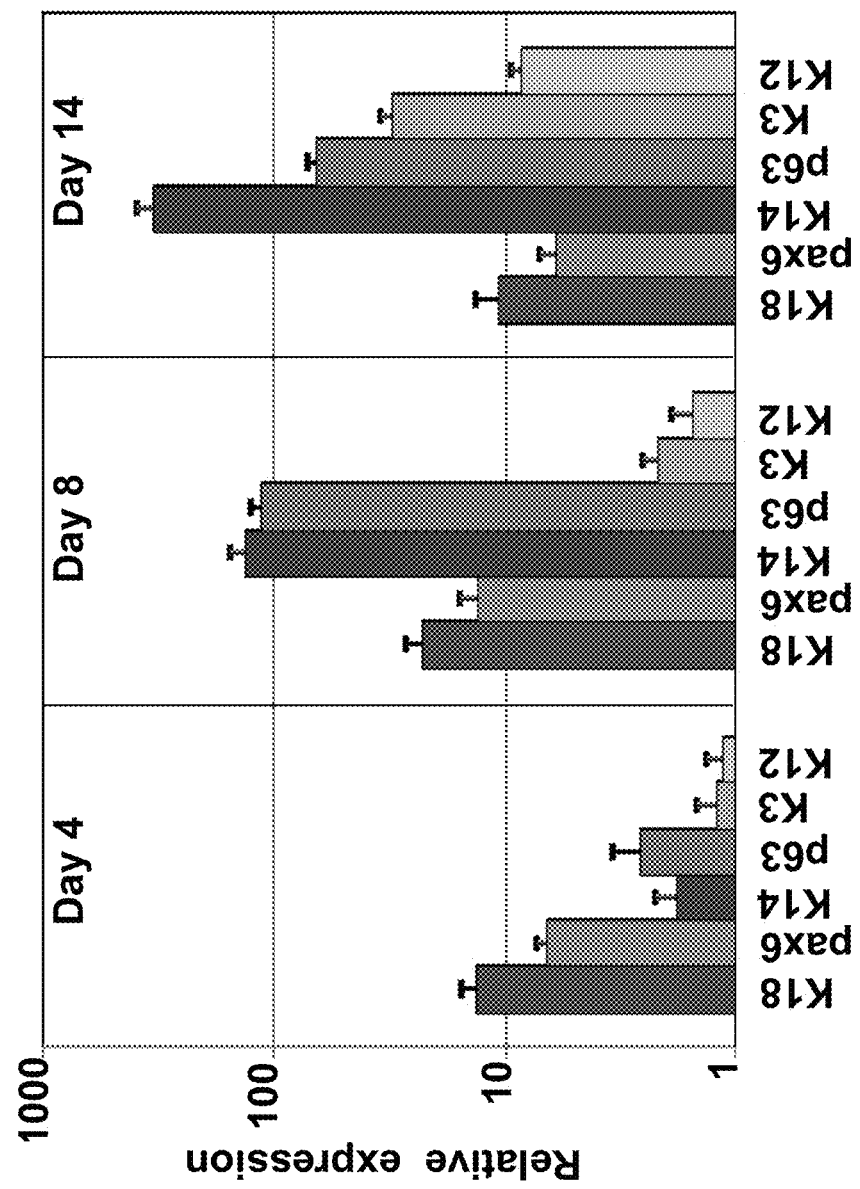
FIGS. 5A-B are photographs illustrating corneal commitment of iPS cell lines.
Figure 5B:
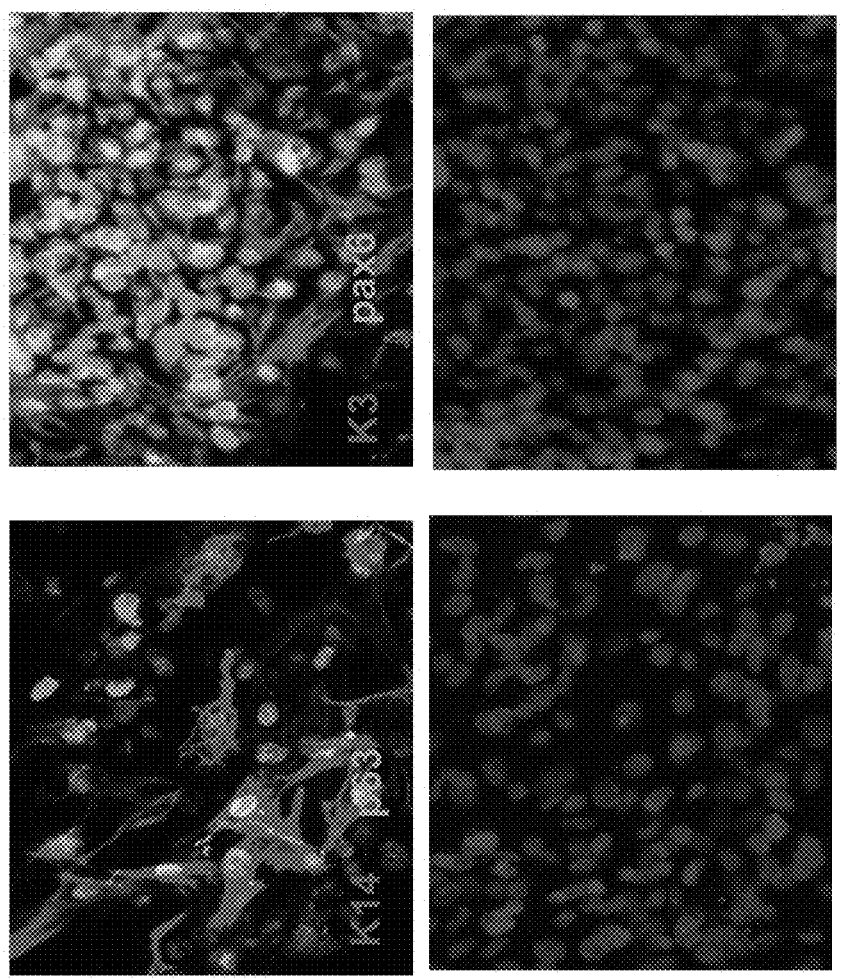
Figure 6A:
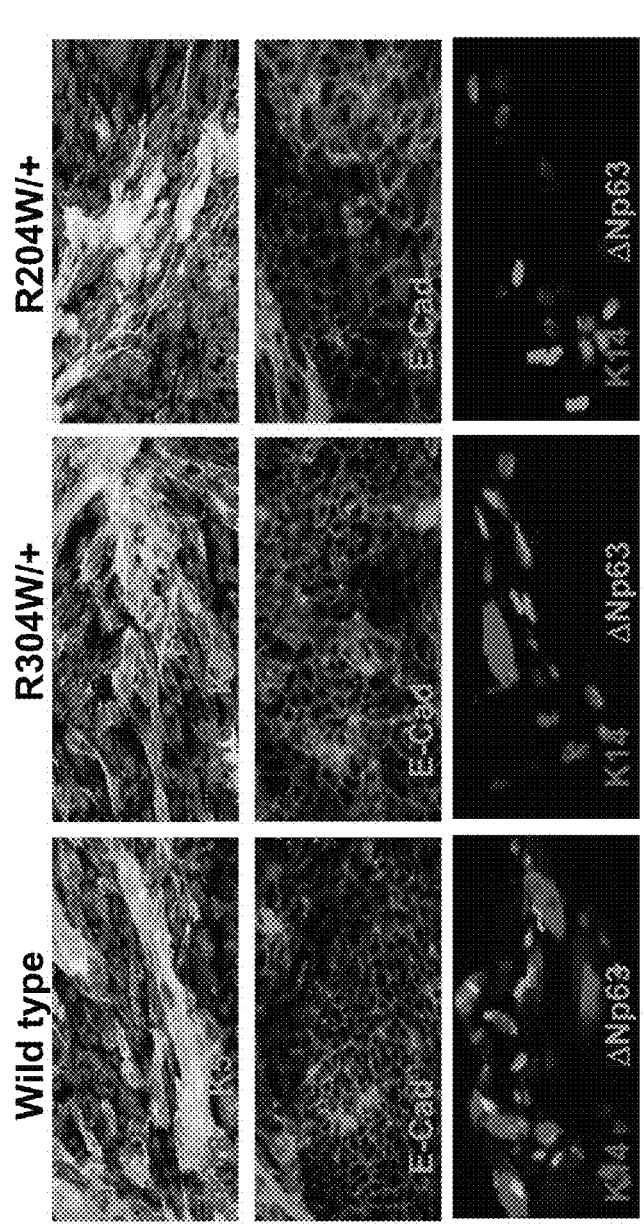
FIGS. 6A-B are photographs and graphs illustrating impaired corneal differentiation of EEC-iPS cells.
Figure 6B:
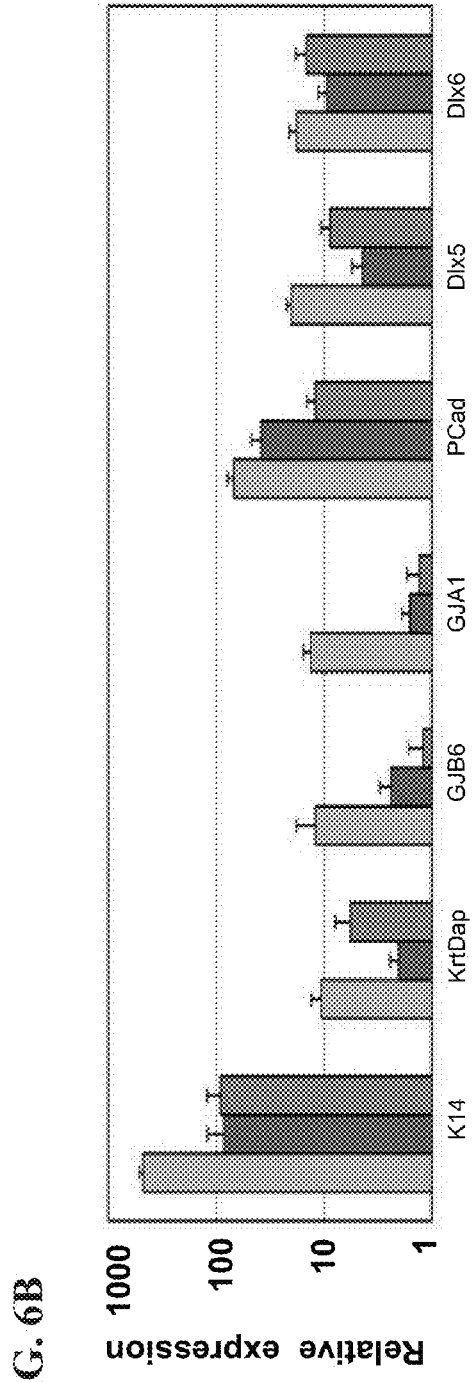

EEC patients suffer from visual morbidity due to impaired cornea associated with limbal stem cell deficiency. iPSC lines were induced to corneal fate as described in Example 3. As illustrated by real-time qRT-PCR analysis, human iPSC lines underwent sequential differentiation into ectodermal precursors (K8/K18+/Pax6$^+$) at day 4, limbal (K14/K5/Pax6$^+$/p63$^+$) at day 8 and corneal epithelial (Pax-6$^+$/K3/K12$^+$) cells at day 14 (FIG. 5A). Remarkably, at day 14, most of the cells became corneal epithelial cells, as detected by immunofluorescent staining (FIG. 5B) and FACS analysis (data not shown). Since EEC patients suffer from limbal stem cell deficiency, iPS$^{EEC}$ cells were challenged for their ability to undergo proper corneal epithelial commitment as compared to the iPSC$^{ctl}$. Immunofluorescent staining analysis was performed at day 10 with antibodies raised against K18, E-cadherin and K14 (FIG. 6A). Similar production of ectodermal progenitors (K18$^+$/E-cadherin$^+$) was observed at day 10 for iPSC$^{ctl}$, iPSC$^{204W}$ and iPSC$^{307W}$. However, the absence of K14 and K3 staining revealed the inability of iPSC$^{EEC}$ to undergo further commitment for the production of limbal cells and corneal cells, respectively, as compared to iPSC$^{ctl}$. In parallel, gene expression of known p63-target genes was evaluated at day 10 of commitment by real-time qRT-PCR (FIG. 6B). Most of the genes were less expressed in mutated cells as compared to control cells.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

---

What is claimed is:

1. A method of generating a population of human corneal epithelial cells comprising culturing human pluripotent stem cells in corneal fibroblast-conditioned medium on a solid surface comprising an extracellular matrix component thereby generating the population of human corneal epithelial cells, wherein said corneal fibroblast-conditioned medium is produced from human corneal fibroblasts which are not contaminated with limbal fibroblasts and comprises insulin, hydrocortisone and epidermal growth factor (EGF).

2. The method of claim 1, wherein said corneal fibroblast-conditioned medium further comprises bone morphogenetic protein-4 (BMP-4).

3. The method of claim 1, wherein said human pluripotent stem cells comprise human embryonic stem cells (hESCs) or human induced pluripotent stem cells (hIPSCs).

4. The method of claim 1, wherein said extracellular matrix component is selected from the group consisting of collagen IV, laminin, fibronectin and Matrigel®.

5. The method of claim 1, further comprising analyzing the population of human corneal epithelial cells for at least one marker selected from the group consisting of keratin 3 (K3), keratin 12 (K12), paired box gene 6 (pax6), keratin 18 (K18) and Connexin 43.

6. A method of generating human corneal tissue, the method comprising:
(a) dissociating a population of human corneal epithelial cells isolated according to the method of claim 1 to generate a population of dissociated human corneal epithelial cells; and
(b) culturing said dissociated human corneal epithelial cells on a scaffold under conditions that generate human corneal tissue.

7. The method of claim 6, wherein said scaffold comprises Matrigel® and collagen I.

8. The method of claim 6, wherein said scaffold comprises a human amniotic membrane.

* * * * *